United States Patent
Schatz et al.

(10) Patent No.: US 6,239,118 B1
(45) Date of Patent: May 29, 2001

(54) METHOD FOR PREVENTING RESTENOSIS USING A SUBSTITUTED ADENINE DERIVATIVE

(76) Inventors: Richard A. Schatz, P.O. Box 8517, Rancho Santa Fe, CA (US) 92067; Alan Saven, 13016 Walking Path Pl., San Diego, CA (US) 92130

( * ) Notice: Subject to any disclaimer, the term of this patent is extended or adjusted under 35 U.S.C. 154(b) by 0 days.

(21) Appl. No.: 09/412,418

(22) Filed: Oct. 5, 1999

(51) Int. Cl.$^7$ .................................................. A61K 31/70
(52) U.S. Cl. ................................................ 514/45; 514/46
(58) Field of Search .......................................... 514/46, 45

(56) References Cited

U.S. PATENT DOCUMENTS

| | | |
|---|---|---|
| 5,106,837 | 4/1992 | Carson et al. . |
| 5,424,296 | 6/1995 | Saven et al. . |
| 5,510,336 | 4/1996 | Saven et al. . |

OTHER PUBLICATIONS

Libby et al, Nouv Rev Fr Hematol, 34 Suppl. S47–53, 1992.*
Faxon, David P., M.D., Chronic Inflamation, *Clinical Trials and Remodeling*; pp. 136–138; University of Southern California School of Medicine, Los Angeles, CA; Restenosis Summit VIII, 1996.
Gerrity, Ross G., PhD. *The Role of the Monocyte in Atherogenesis*, pp. 181 and 191; Research Division, The Cleveland Clinic Foundation, Cleveland, Ohio, Nov. 1, 1980.
Leibovich, S. J. PhD. et al., A Macrophage–Dependent Factor That Stimulates the Proliferation of Fibroblasts in Vitro; *American Journal of Pathology*; pp. 501,508, and 511; Department of Pathology, University of Washington School of Medicine, Seattle, Washington, Apr. 23, 1976.
Ross, Russell, PhD., Mechanism of Disease Atherosclerosis—An Inflammatory Disease, *The New England Journal of Medicine* vol. 340, No. 2, pp. 115–126; Department of Pathology, University of Washington School of Medicine, Seattle, Washington; Jan. 14, 1999.
Ross, Russell, PhD. Medical Progress; The Pathogenesis of Athersclerosis—An Update; *The New England Journal of Medicine* vol. 314, No. 8, pp. 488, 493, 494; Department of Pathololgy, University of Washington School of Medicine, Seattle, Washington; Feb. 20, 1986.
Saven, Alan, M.D., et al.; Brief Communications, 2–Chlorodeoxyadenosine–induced Complete Remissions in Langerhans–Cell Histiocytosis, pp. 430–432; Reprinted from *Annals of Internal Medicine*, vol. 121, No. 6, Sep. 15, 1994.
Schwartz, Stephen M., et al; Remodeling: How Vessels Narrow, *Clinical Trials and Remodeling*; pp. 128–131; University of Washington, Seattle, WA; Massachusetts General Hospital, Boston, MA; and ZymoGenetics, Inc., Seattle WA. 1996.
Waltenberger, Johannes, M.D., Current Perspectives, Modulation of Growth Factor Action, Implications for the Treatment of Cardiovascular Diseases; *Circulation*, pp. 4083–4094; vol. 96, No. 11, Department of Internal Medicine II (Cardiology); Ulm University Medical Center, Ulm, Germany; Dec. 2, 1997.
Copy of Brochure for Leustatin® (cladribine) Injection; Ortho Biotech, Raritan, New Jersey, Dec. 1996.

* cited by examiner

Primary Examiner—Rebecca Cook
(74) Attorney, Agent, or Firm—Nydegger & Associates

(57) ABSTRACT

The present invention discloses a method for the prevention of atherosclerosis, its genesis, progression and restenosis in human patients undergoing treatments for arterial lesions such as PTA or atherectomy, and which may be accompanied by stent implantation. Further, the treatment method disclosed has applicability in all stages of atherosclerosis in which monocytes play a role. The compound utilized in the present method as the active agent is a 2-halo-2'-deoxyadenosine such as 2-chloro-deoxyadenosine (2-CdA). The treatment method of the present invention includes the administration of 14 doses of 2-CdA in the amount of 0.12 mg/kg. One dose is given intravenously before the coronary intervention, another is given intravenously after the intervention and the remaining twelve doses are given subcutaneously at weekly intervals over a subsequent three month period.

15 Claims, No Drawings

METHOD FOR PREVENTING RESTENOSIS USING A SUBSTITUTED ADENINE DERIVATIVE

FIELD OF THE INVENTION

The present invention pertains generally to the prevention of atherosclerosis, its genesis, progression and restenosis following vascular repair. More specifically, the present invention pertains to the administration of a therapeutically effective dose of a substituted adenine derivative to prevent atherosclerosis, its genesis, progression and restenosis following vascular repair. The present invention is particularly, but not exclusively, useful for preventing a restenosis in human patients who have undergone a catheter based procedure, which may include a subsequent stent implantation, to dilate an arterial blockage in the patient's vasculature.

BACKGROUND OF THE INVENTION

Arteriosclerosis, the group of diseases characterized by plaque deposition and gradual blockage of blood flow in arterial vessels, may result in ischemia of the heart, brain or extremities, resulting in infarction and sometimes death. Over 2,000,000 vascular interventions are performed each year worldwide with over 800,000 of these being performed in the United States. Since about 1977, blocked arteries have been treated using a balloon catheter. This procedure, known as percutaneous transluminal angioplasty (PTA), involves the insertion of a catheter into the lumen of a blocked artery and the inflation of an attached balloon to open the artery (both coronary and non-coronary vessels). Another catheter procedure, commonly known as atherectomy, opens a blocked artery by grinding or cutting plaque deposits and suctioning the deposits from the artery. More recently, metal structures called stents have been placed in the affected artery to keep the previously blocked artery open after PTA or atherectomy treatment. Presently, over 70% of persons currently treated for arterial lesions have implanted stents.

It is fortunate that over 90% of coronary interventions are successful in opening the blocked artery. However, the later renarrowing of the opened artery, (i.e. restenosis) remains a significant problem. Unfortunately, within six months after a first PTA or atherectomy treatment, restenosis occurs in about 30% to 50% of patients. When restenosis occurs, either another PTA or atherectomy treatment is performed, and another stent is implanted, or bypass surgery is performed. After a second catheter procedure, restenosis occurs in about 60% of patients, who then must undergo yet another catheter procedure or submit to bypass surgery.

Though many details of restenosis remain unclear, the general consensus is that angioplasty and stenting, either individually or collectively, cause a stretch and tear injury to the arterial wall which results in an inflammation that leads to the activation of multiple cell lines. In particular, there is concern for the monocyte/macrophage line. Specifically, it is known that monocytes will migrate to the area of an arterial injury. There, they differentiate into tissue macrophages and secrete cytokines and growth factors which cause the migration and proliferation of smooth muscle cells into the area. This results in excessive tissue growth or restenosis.

Not surprisingly, efforts have been taken to prevent restenosis. For example, medications such as calcium channel blockers, corticosteroids, antiplatelet agents, fish oils, lovastatin and anticoagulants have been tried in attempts to prevent restenosis. Heretofore, however, these efforts have been generally unsuccessful. Radiation therapy has been shown to reduce restenosis, but radiation therapy is generally impractical because it is time consuming, requires specialized equipment, specialized personnel, and is often difficult to arrange. Some immunosuppressants, on the other hand, show promise.

It is known that the immunosuppressant medication 2-chloro-deoxyadenosine (2-CdA) is selectively toxic to monocytes, and is effective in lowering monocyte levels in humans. Presently, this medication (2-CdA) has been FDA approved for use in the treatment of hairy cell leukemia, and also has activity in cutaneous T-cell lymphoma, myeloid leukemias, chronic lymphocytic leukemia, Langerhans cell histiocytosis and non-Hodgkin's lymphoma. Additionally, FDA approval has been sought for treatment of multiple sclerosis. As a new and useful application, the present invention discloses a method of preventing restenosis by administering a therapeutically effective dose of 2-CdA.

In light of the above, it is an object of the present invention to provide a method for preventing a restenosis in the vasculature of a patient which promotes a systemic suppression to the inflammation response that provokes a restenosis. Another object of the present invention is to provide a method for preventing a restenosis in the vasculature of a patient which uses a medication that can be administered orally, subcutaneously, intravenously, intramuscularly, or topically. Yet another object of the present invention is to provide a method for preventing restenosis in the vasculature of a patient which minimizes adverse side effects and, thus, is minimally intrusive into a patient's life style and quality of life. It is still another object of the present invention to provide a method for preventing a restenosis in the vasculature of a patient which uses a medication that is relatively easy to administer, is effective for its intended purpose, and is comparatively cost effective.

SUMMARY OF THE PREFERRED EMBODIMENT

The present invention discloses a method of treatment for progression of atherosclerosis and the prevention of restenosis in human patients who have submitted to catheter procedures, such as PTA or atherectomy, and who may subsequently require stent implantation in the area of an arterial lesion. In accordance with the present invention, the compound which is utilized as the active agent in the treatment is a 2-halo-2'-deoxyadenosine, which has a structure that corresponds to that of formula:

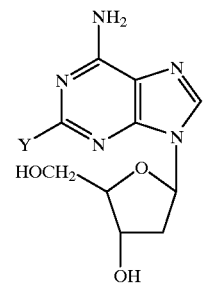

Wherein Y is a halogen, either fluoro, chloro or bromo, but preferably chloro. When Y is chloro, the compound is 2-chloro-deoxyadenosine (2-CdA).

There is general agreement that restenosis is caused by the body's response to the inflammation that is associated with PTA and stent implantation. In this response, monocytes are generated and migrate in the blood to the damaged area of the artery. Once there, the monocytes differentiate into macrophages which, in turn, secrete cytokines and growth factors resulting in the migration and proliferation of the smooth muscle cells that contribute to a restenosis. Administration of 2-CdA, however, is known to kill monocytes and hence lower the monocyte level in humans. In accordance with the present invention, this result is used for the specific purpose of suppressing or preventing a restenosis.

One embodiment of the method of this invention includes the administration of 14 doses of 2-CdA in equal dosages of 0.12 mg/kg of body weight. Prior to the procedure used to obviate the arterial lesion, such as (PTA), the first dose is given. Another dose is given the day following the arterial intervention. The remaining 12 equivalent doses are given thereafter at weekly intervals.

A particular advantage of the present invention is the convenient dosing regimen. Further, as intended for the present invention, dosages can be given either orally in a pill form, intravenously, subcutaneously or intramuscularly with injections, or topically, such as with the use of a carrier. In this aspect, a stent may be used as a carrier. Another advantage of the present invention is that 2-CdA has been FDA approved for the treatment of hairy cell leukemia, thus confirming a substantial safety profile for its use in human patients.

DESCRIPTION OF THE PREFERRED EMBODIMENT

As mentioned above, there is general agreement that catheter procedures such as angioplasty, atherectomy and/or stenting causes a stretch and tear injury to the arterial wall which causes an inflammation. This inflammation leads to the activation of multiple cell lines, and in particular, the monocyte/macrophage line. Monocytes, which are immune cells derived from the bone marrow, migrate to the area of arterial injury, where they differentiate into tissue macrophages and secrete cytokines and growth factors. These cytokines and growth factors then result in restenosis by causing the above normal migration and proliferation of smooth muscle cells into the area. Also, once stimulated, the macrophages secrete a variety of mitogens which stimulate the transformation of smooth muscle cells from their normal contractile state to a secretory state. Further, the macrophages are scavenger cells that can absorb lipids and attack neighboring cells. The net result is an exuberant growth of tissue which encroaches the vessel lumen resulting in restenosis.

In addition to initiating restenosis, monocytes have been implicated in every stage of atherosclerosis from the earliest fatty streaks found in children to the advanced fibromuscular lesions characterized by lipid-laden macrophages, smooth muscle cells, cholesterol crystals, and a fibrous cap. Macrophages are also believed to secrete enzymes called matrix metalloproteinases which lead to thinning and eventual rupture of the fibrous cap causing thrombosis of the coronary artery. Hence, one skilled in the art would recognize that the treatment method disclosed by the present invention may be applicable to every stage of atherosclerosis, and not merely to the prevention of restenosis.

The medication 2-chloro-deoxyadenosine (LEUSTATIN®, Cladribine, or 2-CdA) is a potent immunosuppressant selectively toxic to monocytes and lymphocytes, and is effective in lowering the monocyte levels in humans. Although the exact mechanism by which 2-CdA causes cell death in monocytes is unknown, a mechanism has been established whereby 2-CdA causes cell death in lymphocytes. This mechanism proceeds as follows: 2-CdA in the bloodstream enters the lymphocyte cell, passively crossing the cell membrane. Once inside the lymphocyte cell, 2-CdA is phosphorylated by the lymphocyte enzyme deoxycytidine kinase. Once phosphorylated, the 2-CdA can accumulate in the lymphocyte cell because it is resistant to deamination by adenosine deaminase. Phosphorylated 2-CdA is toxic to lymphocytes by causing impaired DNA synthesis and repair resulting in impaired RNA and protein synthesis and, ultimately, apoptosis or cell death.

This medication, 2-CdA, has been FDA approved for use in the treatment of hairy cell leukemia, and has activity in cutaneous T-cell lymphoma, myeloid leukemias, chronic lymphocytic leukemia, langerhans cell histiocytosis and non-Hodgkin's lymphoma. Further, FDA approval has been sought for the use of 2-CdA in the treatment of multiple sclerosis. Use of 2-CdA in the above listed treatments has generated a favorable safety profile for use in humans.

Hence, the present invention discloses a method of preventing atherosclerosis, its genesis, progression and restenosis by administering a therapeutically effective dose of 2-CdA to temporarily lower the monocyte level in the blood and specifically near the area of arterial inflammation. Lowering the monocyte level for a three month period following coronary intervention is preferred.

One embodiment of the method of the present invention includes the administration of 14 doses of 2-CdA in a pharmacologically acceptable carrier or a pharmacologically acceptable acid addition salt of 2-CdA to the patient. As summarized in the following table, an exemplary therapeutic dosage of 0.12 mg/kg of body weight is given prior to the catheter procedure used to obviate the arterial lesion. An equivalent second dose is given one day subsequent to the procedure, and the remaining 12 equivalent doses are given thereafter at weekly intervals.

| Dose (mg/kg of body weight) | Method of Administration | Time of Administration |
| --- | --- | --- |
| 0.12 | Intravenously | Prior to Catheter Procedure |
| 0.12 | intravenously | Day After Catheter Procedure |
| 0.12 | Subcutaneously | Qne week after Catheter Procedure |
| 0.12 | Subcutaneously | Two weeks after Catheter Procedure |
| 0.12 | Subcutaneously | Three weeks after Catheter Procedure |
| 0.12 | Subcutaneously | Four weeks after Catheter Procedure |
| 0.12 | Subcutaneously | Five weeks after Catheter Procedure |
| 0.12 | Subcutaneously | Six weeks after Catheter Procedure |
| 0.12 | Subcutaneously | Seven weeks after Catheter Procedure |
| 0.12 | Subcutaneously | Eight weeks after Catheter Procedure |
| 0.12 | Subcutaneously | Nine weeks after Catheter Procedure |
| 0.12 | Subcutaneously | Ten weeks after Catheter Procedure |
| 0.12 | Subcutaneously | Eleven weeks after Catheter Procedure |
| 0.12 | Subcutaneousiy | Twelve weeks after Catheter Procedure |

Although the 2-CdA could be administered in several ways including orally, topically, subcutaneously, intravenously or intramuscularly, it is practical to administer the first two dosages intravenously since the recipient is generally a hospital patient when the dosage is required, while the remaining dosages are given subcutaneously by medical personnel at outpatient clinics or in the home.

While the particular method as herein disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for preventing a restenosis at a location of an inflammation in the vasculature of a patient which comprises the steps of:

apportioning a medicament into a plurality of therapeutically effective doses, wherein said medicament is selected from a group consisting of a substituted adenine derivative and a pharmacologically acceptable acid addition salt thereof, said medicament having the formula:

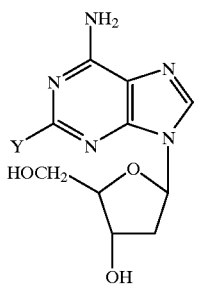

wherein Y is a halogen, each said dose of said medicament being efficacious for responding to said inflammation by reducing monocytes in the blood to below a preselected level; and administering at least one of said doses to a human in accordance with a predetermined regimen.

2. The method as recited in claim 1 wherein Y is chlonine.

3. The method as recited in claim 1 wherein said inflammation results from a catheter procedure.

4. The method as recited in claim 3 wherein said catheter procedure is a percutaneous transluminal angioplasty (PTA) procedure.

5. The method as recited in claim 3 wherein said catheter procedure is selected from a group consisting of an atherectomy procedure, a photolysis procedure and a radio frequency ablation procedure.

6. The method as recited in claim 3 wherein said catheter procedure includes implantation of an arterial stent.

7. The method as recited in claim 1 wherein said predetermined regime comprises the steps of:

preparing fourteen individual portions of said medicament;

administering a first said portion of said medicament to said human prior to a catheter procedure;

administering a second said portion of said medicament to said human subsequent said catheter procedure; and administering one of said remaining twelve portions of said medicament at consecutive weekly intervals over a twelve week period immediately following said administering of said second said portion of said medicament.

8. The method as recited in claim 7 wherein said first portion of said medicament is administered on the day of said catheter procedure and said second portion of said medicament is administered on the day immediately following said catheter procedure.

9. The method as recited in claim 7 wherein each said portion of said medicament is approximately one twelve hundredths of a milligram per kilogram of body weight (0.12 mg/Kg).

10. The method as recited in claim 7 wherein said first and second portions of said medicament are administered intravenously, and said remaining portions are administered subcutaneously.

11. A method for reducing the production of monocytes in a patient to prevent a restenosis wherein said method comprises the steps of:

preparing fourteen individual portions of a medicament, wherein said medicament is selected from a group consisting of a substituted adenine derivative and a pharmacologically acceptable acid addition salt thereof, said medicament having the formula:

wherein Y is a halogen;

administering a first said portion of said medicament to said human prior to a catheter procedure;

providing a second said portion of said medicament to said human subsequent said catheter procedure; and dispensing one of said remaining twelve portions of said medicament at consecutive weekly intervals over a twelve week period immediately following said administering of said second said portion of said medicament.

12. The method as recited in claim 11 wherein said first portion of said medicament is administered on the day of said catheter procedure and said second portion of said medicament is administered on the day immediately following said catheter procedure.

13. The method as recited in claim 11 wherein each said portion of said medicament is approximately one twelve hundredths of a milligram per kilogram of body weight (0.12 mg/Kg).

14. The method as recited in claim 11 wherein said first and second portions of said medicament are administered intravenously, and said remaining portions are administered subcutaneously.

15. The method as recited in claim 11 wherein Y is chlorine.

* * * * *